United States Patent [19]

Tanaka et al.

[11] 4,139,548

[45] Feb. 13, 1979

[54] METHYLDI(TRIMETHYLSILOXY)SYLYL-PROPYLGLYCEROL METHACRYLATE

[75] Inventors: Kyoichi Tanaka; Kouzou Takahashi, both of Nagoya; Mitsuhiro Kanada, Aichi; Toshiharu Yoshikawa, Nagoya, all of Japan

[73] Assignee: Toyo Contact Lens Co., Ltd., Aichi, Japan

[21] Appl. No.: 888,315

[22] Filed: Mar. 20, 1978

[30] Foreign Application Priority Data

Oct. 20, 1977 [JP] Japan ............................. 52-126427

[51] Int. Cl.$^2$ ............................................. C07F 7/08
[52] U.S. Cl. ............................................. 260/448.2 B
[58] Field of Search ................................. 260/448.2 B

[56] References Cited

U.S. PATENT DOCUMENTS

| | | | |
|---|---|---|---|
| 3,746,734 | 7/1973 | Berger et al. | 260/448.2 B |
| 3,878,263 | 4/1975 | Martin | 260/448.2 B X |
| 3,965,150 | 6/1976 | Moeller | 260/448.2 B X |

*Primary Examiner*—Paul F. Shaver
*Attorney, Agent, or Firm*—Armstrong, Nikaido, Marmelstein & Kubovcik

[57] ABSTRACT

A novel methacrylic acid ester derivative, methyldi(trimethylsiloxy)sylylpropylglycerol methacrylate which is availably employed as a main monomer for preparing copolymers useful as a material of contact lenses. The derivative has siloxane bond which contributes to increase of the oxygen permeability of its copolymers, and has hydrophilic hydroxyl group and ether bond by which the derivative is miscible with a hydrophilic monomer in all proportions and is easily copolymerizable therewith and colorless transparent copolymers are obtained.

1 Claim, 2 Drawing Figures

METHYLDI(TRIMETHYLSILOXY)SYLYL-PROPYLGLYCEROL METHACRYLATE

BACKGROUND OF THE INVENTION

The present invention relates to a novel compound, and more particularly to methyldi(trimethylsiloxy)-sylylpropylglycerol methacrylate which is availably employed as a main monomer for preparing copolymers useful as a material of contact lenses.

Contact lenses made of polymethyl methacrylate are well known. These contact lenses have the disadvantages that the oxygen permeability is low and the hydrophilic property is poor. Therefore, since cornea is easy to fall into a state of oxygen starvation, and also since the contact lens lacks in affinity for cornea and gives a foreign body sensation, it takes about one month for accomodation and even if persons have accomodated to wear of the contact lenses, they cannot wear over 12 hours in a day.

In order to eliminate such disadvantages of the contact lenses made of polymethyl methacrylate, there have been proposed high water content lenses made of a polymer of ethylene glycol monomethacrylate as a main component. These contact lenses have a higher oxygen permeability than that of the contact lenses made of polymethyl methacrylate, but cannot permeate a sufficient amount of oxygen for cornea. Also, these contact lenses have the fatal disadvantage of being contaminated by bacteria, because the water content is too high.

OBJECTS OF THE INVENTION

It ia an object of the present invention to provide a novel methacrylic acid ester derivative which can be availably employed as a monomer for preparing copolymers useful as a material of contact lenses.

A further object of the invention is to provide a polymerizable compound having a siloxane bond which contributes to increase of the oxygen permeability of obtained polymers.

A still further object of the invention is to provide a copolymerizable compound having the excellent miscibility with a hydrophilic monomer.

Another object of the invention is to provide a copolymerizable compound suited for preparing contact lenses which have the excellent oxygen permeability and the affinity for cornea and can be worn continuously for a long term without giving a foreign body sensation.

These and other objects of the invention will become apparent from the description hereinafter.

DETAILED DESCRIPTION

Figure 1:
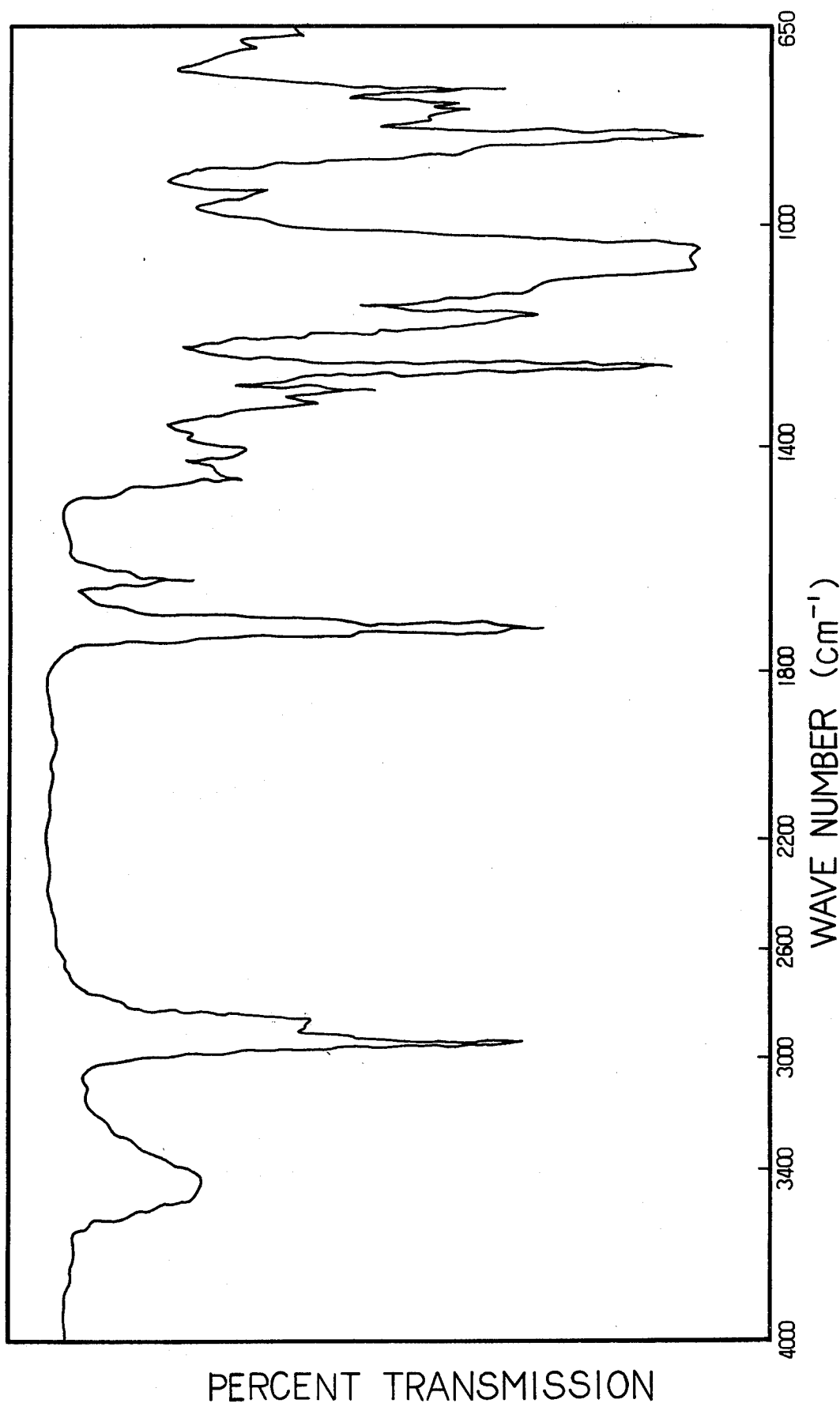
FIG. 1 is the infrared absorption spectrum of the compound of the present invention.

It has now been found that the above-mentioned objects can be attained by a novel compound, i.e. methyldi(trimethylsiloxy)sylylpropylglycerol methacrylate having the following formula (I):

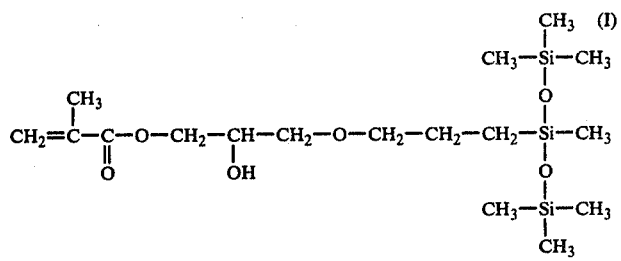

The novel compound of the present invention is prepared by reacting methyldi(trimethylsiloxy)sylylpropyl(oxypropylene oxide (hereinafter referred to as "SiPO") having the following formula (II):

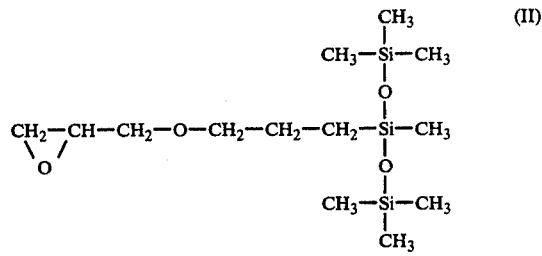

with methacrylic acid in the presence of a catalyst such as potassium hydroxide, trimethylbenzylammonium chloride, triethylbenzylammonium chloride or triethylamine.

The reaction is generally carried out at a temperature of 80° to 105° C. for 6 to 8 hours. In order to prevent the polymerization of methacrylic acid, it is desirable to carry out the reaction in the presence of a polymerization inhibitor, while replacing air with nitrogen gas. Examples of the polymerization inhibitor are hydroquinone, hydroquinone monomethyl ether and sulfur, and hydroquinone is suitably employed due to the easiness of the removal after the completion of the reaction.

Although the reaction between SiPO and methacrylic acid is equimolar reaction, it is effective to employ 1.5 to 2.5 moles of methacrylic acid per mole of SiPO, since more than 99% of the employed SiPO can be made to react with methacrylic acid. In that case, excess methacrylic acid is removed by washing with an aqueous solution of sodium hydroxide after the completion of the reaction.

Since the product is a polymerizable, viscous, high-boiling material, it is difficult to utilize recrystallization or distillation procedure for purification, and the reaction product is usually purified by washing. The washing may be conducted by directly pouring an aqueous solution of sodium hydroxide to the reaction mixture, but the separation is difficult and, therefore, preferably the reaction mixture is first dissolved in n-hexane and then washed with an aqueous solution of sodium hydroxide. It is suitable to employ n-hexane in an amount of about 9 times the volume of the reaction mixture. The washing is usually conducted in a separatory funnel by employing the washing liquid in a volume approximately equal to the mixture of the reaction mixture and n-hexane. The under layer is the washing liquid which dissolves methacrylic acid and hydroquinone. After removing the under layer, the above washing procedure is repeated until no coloration based on the presence of hydroquinone is observed. In general, the above washing procedure is repeated 3 to 5 times. Since the thus washed mixture of the reaction mixture and n-hexane contains a small quantity of alkali, the mixture is further washed with water or a saline water to remove alkali. The use of a saline water is preferred, since the separation is easy. The washing with water or a saline water is repeated, usually 3 to 5 times, until the washing liquid becomes neutral. After washing the mixture, a small quantity of water included in the mixture is removed by employing a drying agent such as anhydrous sodium sulfate or Glauber's salt. After filtration, n-hexane is distilled away, for instance, by employing an evaporator. The removal of n-hexane by an evaporator is suitably carried out first by maintaining the temperature of a water bath at about 50° C., secondary at the same temperature with suction by means of an aspirator, and then at about 65° C. under a reduced pressure of 5 to 10 mmHg for about one hour by employing a vacuum pump.

The thus obtained novel compound of the present invention has the following features from the structural point of view, as is also apparent from the formula (I).

1. The compound has siloxane bond at the molecular end. The siloxane bond contributes to increase of the oxygen permeability of its copolymers.
2. The compound has double bond and, therefore, is copolymerizable with other unsaturated hydrocarbons.
3. The compound has hydroxyl group and ether bond in the molecule, which are hydrophilic. Therefore, the compound is miscible with hydrophilic monomers in all proportions and is easily copolymerizable therewith, and the obtained copolymers are colorless and transparent.

The compound of the present invention can be availably employed as a monomer for preparing copolymers useful as a material of contact lenses. When the compound of the invention is copolymerized with other particular monomers such as a hydrophilic monomer, there can be obtained copolymers suitable for use as a material of contact lenses which have the excellent oxygen permeability and the affinity for cornea and can be worn continuously for a long term without giving a foreign body sensation. For instance, when 30 to 80% of the compound of the invention is copolymerized with 5 to 30% of a hydrophilic monomer such as ethylene glycol monomethacrylate or diethylene glycol menomethacrylate, 5 to 60% of an alkyl methacrylate such as methyl methacrylate or ethyl methacrylate, and 0.5 to 15% of a cross-linking agent having at least two copolymerizable functional groups such as ethylene glycol dimethacrylate or diethylene glycol dimethacrylate (the above all % being % by weight based on the total weight of the reactants), in the presence of a radical polymerization initiator such as azobisisobutyronitrile or azobisdimethylvaleronitrile by means of a bulk polymerization, the produced copolymers have the excellent processing property upon the preparation of contact lenses therefrom, and the obtained contact lenses have a high oxygen permeability and the excellent affinity for cornea and can be worn continuously for a long term without giving a foreign body sensation.

The present invention is more particularly described and explained by means of the following Example.

EXAMPLE 1

[Preparation of methyldi(trimethylsiloxy)sylylpropylglycerol methacrylate (hereinafter referred to as "SiGMA") of the present invention]

A one liter round bottom flask equipped with a magnetic stirrer, a thermometer, a tube for introducing nitrogen gas, a dropping funnel and a reflux condenser was charged with 336 g. of SiPO, 6.9 g. of potassium hydroxide and 0.8 g. of hydroquinone, and was placed on an oil bath. With introducing nitrogen gas into the flask, 172 g. of methacrylic acid was added dropwise to the flask through the dropping funnel with stirring over about 30 minutes. The mixture was then gradually heated to 100° C. and at this temperature the reaction was carried out for about 7 hours. After the completion of the reaction, the reaction mixture was allowed to cool and filtered to remove potassium methacrylate. The filtrate was then admixed with n-hexane in an amount of about 9 times the volume of the filtrate and the mixture was washed several times with a 0.5N aqueous solution of sodium hydroxide to remove the excess methacrylic acid and hydroquinone by employing a separatory funnel, until the aqueous solution became colorless. The mixture was further washed several times with a saline water to remove sodium hydroxide remaining in the mixture. The thus washed mixture was then placed in an Erlenmeyer flask and was dehydrated by employing anhydrous sodium sulfate for a day and night. After removing anhydrous sodium sulfate by filtration, n-hexane was distilled away by an evaporator, first at 50° C., then at 50° C. with suction by an aspirator and further at 65° C. with reducing a pressure to 10 mmHg by a vacuum pump.

Figure 2:
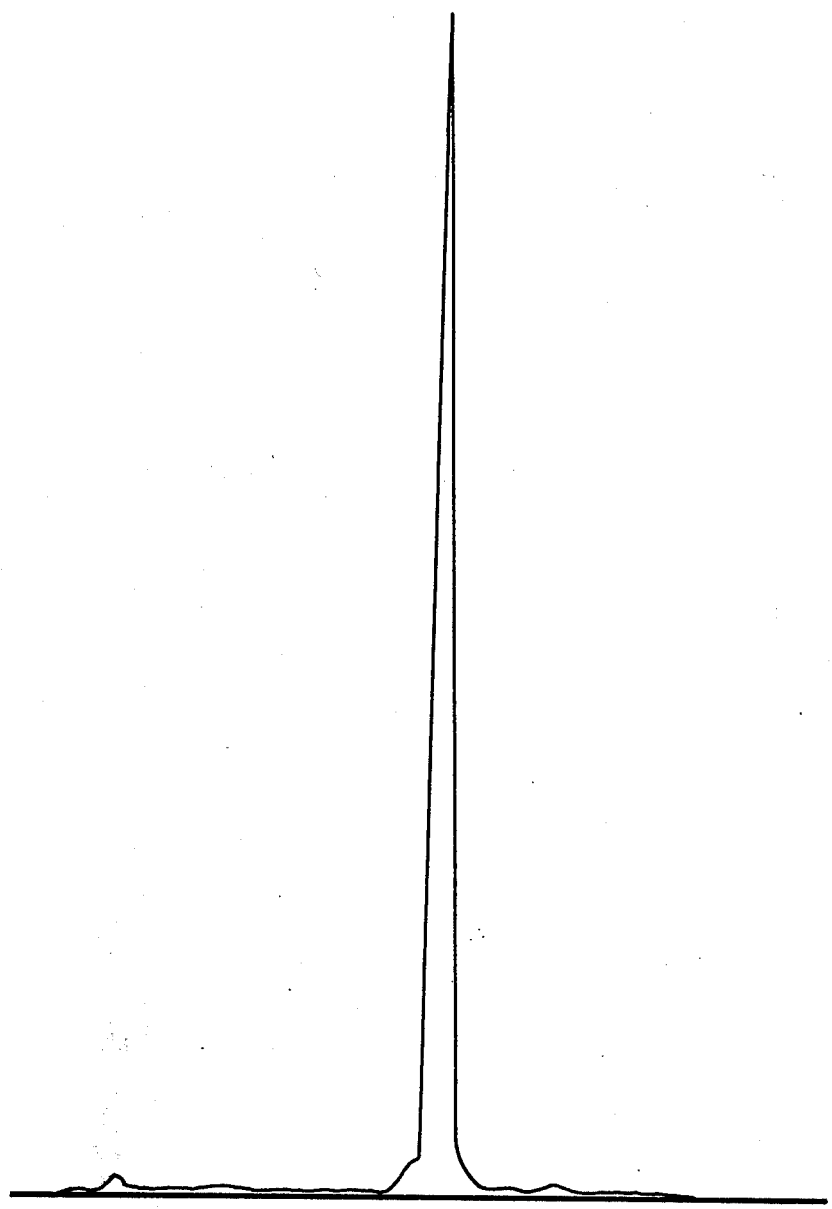
FIG. 2 is the gas chromatogram of the compound of the present invention.

The thus obtained reaction product was a slightly viscous, transparent liquid. According to the quantitative analysis by gas chromatography, the purity of the obtained product was 98.7%. Also, the refractive index $n_D^{20}$ of the product was 1.440. The infrared absorption spectrum of the product indicated absorptions of hydroxyl group at 3,420 cm.$^{-1}$, of double bond at 1,640 cm.$^{-1}$, of ester bond at 1,720 cm.$^{-1}$, of Si-O-Si bond at 1,040 cm.$^{-1}$ and 1,080 cm.$^{-1}$, of methyl group at 2,950 cm.$^{-1}$, 1,400 cm.$^{-1}$ and 1,300 cm.$^{-1}$, and of —Si—$(CH_3)_3$ group at 845 cm.$^{-1}$ No absorption of epoxy group at 910 cm.$^{-1}$ was observed. The infrared absorption spectrum and the gas chromatogram of the product are shown in FIG. 1 and FIG. 2, respectively.

The result of the elemental analysis was as follows:
Calculated for $C_{17}H_{38}O_6Si_3$: C 48.3%; H 9.0%
Found: C 49.7%; H 9.3%

From the above results, it was confirmed that the product was SiGMA. [Preparation of copolymer and contact lenses therefrom]

By employing the thus obtained SiGMA, a copolymer was prepared as follows:

Fifty-five grams of SiGMA, 10 g. of ethylene glycol monomethacrylate, 5 g. of ethylene glycol dimethacrylate, 30 g. of methyl methacrylate and 0.08 g. of azobisdimethylvaleronitrile were thoroughly admixed and then placed in a test tube. Under the ultraviolet irradiation, the polymerization was carried out stepwise at 15° C. for 16 hours, at 40° C. for 8 hours and at 50° C. for 8 hours, and then the ultraviolet irradiation was stopped and the thermal polymerization was further carried out stepwise at 60° C. for 24 hours, at 80° C. for 4 hours, at 100° C. for 4 hours and at 120° C. for 4 hours, to give a colorless, transparent rod.

From the thus obtained material for contact lens in the form of rod, a piece having a diameter of 15 mm. and a thickness of 0.1 mm. was obtained by mechanical processing, and the oxygen permeability was measured by an oxygen gas permeameter made by Rikaseiki Kogyo Co., Ltd. The oxygen permeability was $14.9 \times 10^{-1}$ ml.cm./cm.$^2$sec.cmHg. Also, the material had a refractive index $n_D^{20}$ of 1.4761 which was measured by Abbé's refractometer made by Erma Optical Works Co., Ltd., a specific gravity of 1.11 and a visible ray percent transmission of 97.8% which are measured by Double-Beam Spectro Photometer UV-210 made by Shimadzu Seisakusho Ltd. by employing the material having a thickness of 0.15 mm.

The material in the form of rod was subjected to a usual mechanical processing such as cutting, grinding and polishing to give contact lenses having a base-curve of 7.90 mm., a front-curve of 8.10 mm., a center thickness of 0.13 mm. and a size of 11.5 mm. The thus prepared contact lenses were worn on rabbit eyes continuously for 21 days. No change was observed on the eyes. Also, the contact lens had good hydrophilic property.

The judgement of the hydrophilic property was conducted by immersing the contact lens in a 0.9% saline water and observing whether or not the surface of the contact lens was covered with the water when the contact lens was picked out with tweezers. When the contact lens was covered with the water, the hydrophilic property of the lens was judged as good.

What we claim is:

1. A compound of the formula:

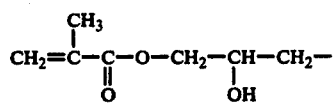

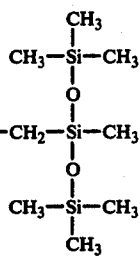

* * * * *